(12) United States Patent
Stone

(10) Patent No.: US 7,440,121 B2
(45) Date of Patent: Oct. 21, 2008

(54) OPTICALLY MEASURING INTERIOR CAVITIES

(75) Inventor: Gary Franklin Stone, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 177 days.

(21) Appl. No.: 11/524,648

(22) Filed: Sep. 20, 2006

(65) Prior Publication Data

US 2008/0068600 A1    Mar. 20, 2008

(51) Int. Cl.
  *G01N 21/00* (2006.01)
(52) U.S. Cl. .................. 356/627; 356/626; 356/635; 250/227.2; 250/559.19
(58) Field of Classification Search ... 356/241.1–241.6, 356/436, 626–630, 635–636; 250/234, 549, 250/216, 227.2, 559.19, 559.22; 600/160, 600/410, 474
See application file for complete search history.

(56) References Cited

U.S. PATENT DOCUMENTS

| | | | | |
|---|---|---|---|---|
| 4,558,691 A * | 12/1985 | Okada | ........................ | 600/117 |
| 4,595,479 A * | 6/1986 | Kimura et al. | ............... | 204/294 |
| 4,660,982 A * | 4/1987 | Okada | ........................ | 356/636 |
| 4,784,144 A * | 11/1988 | Ono et al. | ................... | 600/325 |
| 5,130,254 A * | 7/1992 | Collier et al. | ................. | 436/54 |
| 5,432,543 A | 7/1995 | Hasegawa et al. | | |
| 5,823,942 A * | 10/1998 | Toida | ......................... | 600/160 |
| 5,895,927 A * | 4/1999 | Brown | .................. | 250/559.19 |
| 6,009,189 A | 12/1999 | Schaack | | |
| 6,137,582 A * | 10/2000 | Stedham | ..................... | 356/436 |
| 6,226,085 B1 * | 5/2001 | Weber | ......................... | 356/600 |
| 6,295,368 B1 | 9/2001 | Hasegawa et al. | | |
| 6,434,413 B1 * | 8/2002 | Liu et al. | .................... | 600/410 |
| 6,459,481 B1 | 10/2002 | Schaack | | |
| 6,472,660 B1 * | 10/2002 | Hother | ..................... | 250/269.1 |
| 6,639,739 B1 | 10/2003 | Stone et al. | | |
| 6,929,604 B2 | 8/2005 | Stone et al. | | |
| 7,139,473 B2 * | 11/2006 | Shimano et al. | ................ | 396/73 |

FOREIGN PATENT DOCUMENTS

GB    2301680    11/1996

* cited by examiner

*Primary Examiner*—Sang Nguyen
(74) *Attorney, Agent, or Firm*—Eddie E. Scott; John H. Lee

(57) ABSTRACT

A method of measuring the three-dimensional volume or perimeter shape of an interior cavity includes the steps of collecting a first optical slice of data that represents a partial volume or perimeter shape of the interior cavity, collecting additional optical slices of data that represents a partial volume or perimeter shape of the interior cavity, and combining the first optical slice of data and the additional optical slices of data to calculate of the three-dimensional volume or perimeter shape of the interior cavity.

1 Claim, 5 Drawing Sheets

OPTICALLY MEASURING INTERIOR CAVITIES

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to measuring and more particularly to optically measuring interior cavities.

2. State of Technology

U.S. Pat. No. 5,432,543 issued Jul. 11, 1995 to Jun Hasegawa et al for endoscopic image processing device for estimating three-dimensional shape of object based on detection of same point on a plurality of different images provides the following state of technology information: "When the relative arrangement of the imaging means disposed with overlap in a visual field is known, various methods are known which estimate the shape of an object from the images formed, i.e., for estimating the shape from stereo-images. In recent years, some methods have also been proposed for determining a three-dimensional structure from information about the movement of an object. The methods employ the technique of estimating the relative movement of imaging means from a plurality of images."

U.S. Pat. No. 6,009,189 issued Dec. 28, 1999 to David F. Schaack for apparatus and method for making accurate three-dimensional size measurements of inaccessible objects provides the following state of technology information: "In the past several decades, the use of optical endoscopes has become common for the visual inspection of inaccessible objects, such as the internal organs of the human body or the internal parts of machinery. These visual inspections are performed in order to assess the need for surgery or equipment tear down and repair; thus the results of the inspections are accorded a great deal of importance."

U.S. Pat. No. 6,459,481 issued Oct. 1, 2002 to David F. Schaack for simple system for endoscopic non-contact three-dimensional measurement provides the following state of technology information: "Making accurate dimensional measurements of objects viewed through endoscopes is important to aerospace as well as other industries in which expensive equipment must undergo periodic internal inspections to maintain safe operation. Such measurements also have medical applications, where the internal condition of a patient is evaluated prior to or during surgery by viewing through an endoscope. The fundamental problems in making an accurate measurement through an endoscope are that the magnification of the image varies rapidly with the range of the object, and that objects of interest (defects) lie on surfaces which are curved in three dimensions; thus the magnification varies from one point on the object to another. What is needed is a fully three-dimensional measurement, that is, one which determines the depth, as well as the height and width, of an object. Endoscopes are long and narrow optical systems, typically circular in cross-section, which can be inserted through a small opening in an enclosure to give a view of the interior. They almost always include a source of illumination which is conducted along the interior of the scope from the outside (proximal) end to the inside (distal) end, so that the interior of the chamber can be viewed even if it contains no illumination. Endoscopes are divided into two basic types: these are the rigid "borescopes" and the flexible "fiberscopes" or "videoscopes.""

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a method of measuring the three-dimensional volume or perimeter shape of an interior cavity. The method includes the steps of collecting a first optical slice of data that represents a partial volume or perimeter shape of the interior cavity, collecting additional optical slices of data that represents a partial volume or perimeter shape of the interior cavity, and combining the first optical slice of data and the additional optical slices of data to calculate of the three-dimensional volume or shape of the interior cavity.

The present invention has use in industrial and medical applications. Uses in industrial applications include measuring the interior volume of small gas/liquid valves or odd shaped gas/liquid reservoirs to accurately determine the amount of a fluid that is present within a liquid delivery system. Knowing the amount of gas/fluid within odd shaped valve will improve the accuracy of delivery of toxic, rare or expensive fluid mixtures. In the medical field, the present invention can be used to measure the amount of tissue removed in a spinal discectomy procedure or the amount of bone marrow removed during a marrow transplant procedure. The present invention can also be used to map the interior shape and size of the hole generated during a hip or knee replacement. With an accurate measure of the interior of the receiving hole for a prosthesis, that data can be fed into a computer numerical machining mill to improve the fit of the device.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
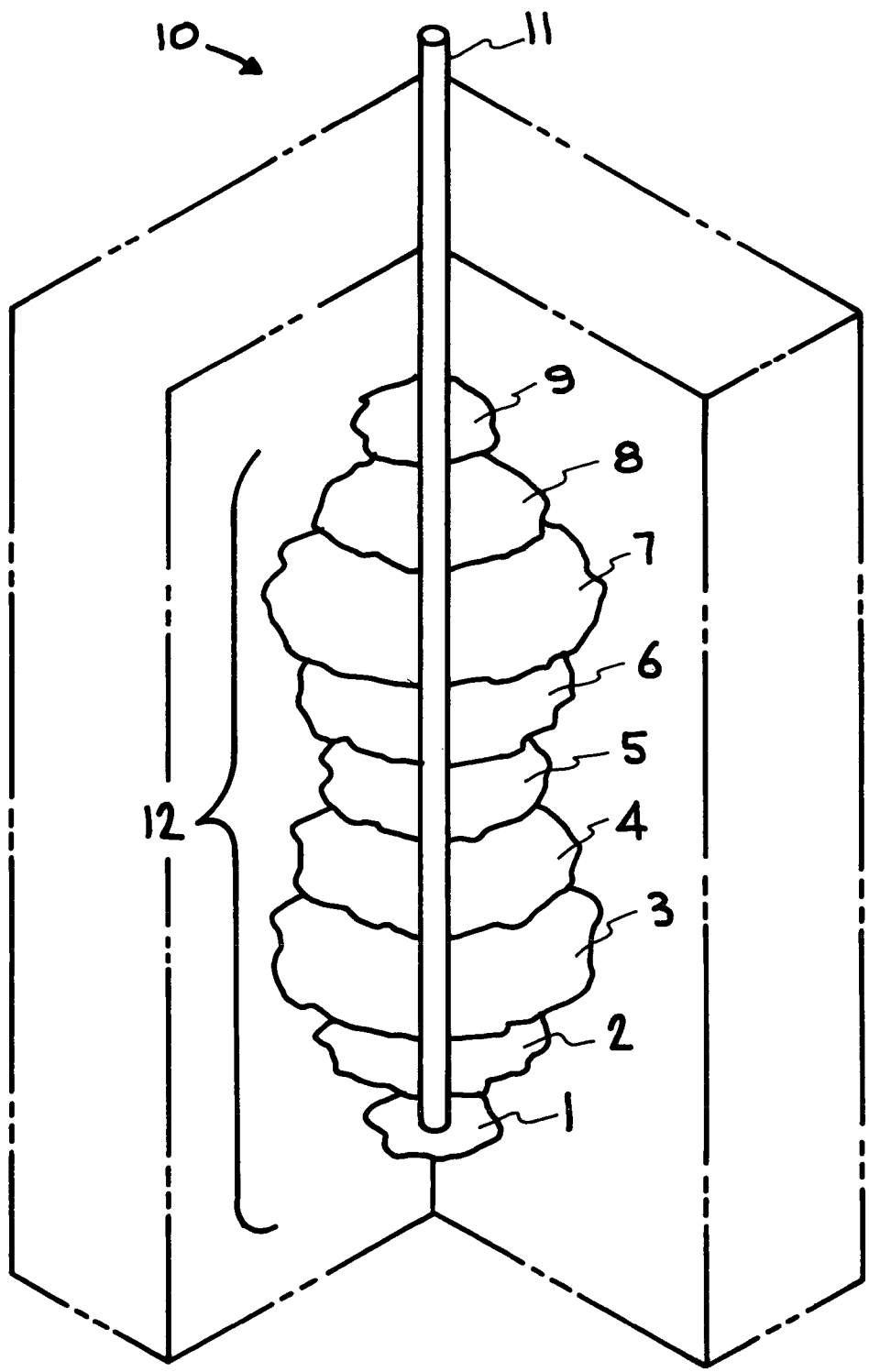
FIG. 1 illustrates a system for measuring the three-dimensional volume and perimeter shape of an interior cavity of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The fundamental problems in making an accurate measurement through an endoscope are that the magnification of the image varies rapidly with the angular position within the image field of view, and that objects of interest (defects) lie on surfaces which are curved in three dimensions; thus the magnification within an image varies from one point on the object to another. What is needed is a fully three-dimensional measurement, that is, one which determines the depth, as well as the height and width, of an object.

Endoscopes are long and narrow optical systems, typically circular in cross-section, which can be inserted through a small opening in an enclosure to give a view of the interior. They almost always include a source of illumination which is conducted along the interior of the scope from the outside (proximal) end to the inside (distal) end, so that the interior of the chamber can be viewed even if it contains no illumination. Endoscopes are divided into two basic types: these are the rigid "borescopes" and the flexible "fiberscopes" or "videoscopes". The rigid borescopes are generally designed to view in a direction along the mechanical axis of the instrument. Fiberoptic endoscopes are made in both the single point of view style as are borescopes as well as a single of multiple axis steerable style. Flexible endoscopes are built with a variety of mechanical components to change the direction of a portion of the distal end to change the viewing direction.

Referring now to the drawings and in particular to FIG. 1, a system for measuring the three-dimensional volume and perimeter shape of an interior cavity of the present invention is illustrated. The system is designated generally by the reference numeral 10. The system 10 provides a non-contact method to measure the interior perimeter shape and/or volume of irregular shaped cavities useful for industrial and medical applications. The system will enable accurate determination of the amount of material removed during a medical procedure or the shape and volume of an interior cavity that has been machined or chemically etched within a semi-closed space. This will improve both the medical and industrial processes by giving more precise measurements The system 10 includes a method utilizing the steps of collecting a first optical slice of data that represents a partial volume of an interior cavity 12, collecting additional optical slices of data that represents a partial volume of the interior cavity 12, and combining the first optical slice of data and the additional optical slices of data to calculate the three-dimensional volume of the interior cavity 12. The system 10 also provides a method of determining the interior perimeter shape of the cavity 12.

As illustrated in FIG. 1, the system 10 utilizes a high resolution, low optical distortion, narrow depth of field rigid fiberscope or flexible endoscope 11 to collect optical slices of data that represents a partial volume of the interior cavity 12. The optical element at the distal end of the instrument has been designed to collect an image with a finite, limited depth of field or range of good image focus along the optical axis of the instrument. This shallow optical depth of field is key to the process of accurately measuring the interior volume of a three dimensional cavity. The present invention provides a method for the collection of a series of thin optical depth images, at known positions along the optical axis. A first optical slice of data that represents a partial volume of the interior cavity 12 is designated by the reference numeral 1. The additional optical slices of data that represents a partial volume of the interior cavity 12 are designated by the reference numerals 2-9.

The first optical slice of data 1 is an optical slice of data taken at a known interval, relative to a fixed starting position, and with a finite measured optical depth of focus of the optical rigid fiberscope or flexible endoscope 11. As the image will have a shallow depth of focus, only a thin portion of the image will be in good or acceptable focus. It is the image portion that is in focus that defines the perimeter of the interior volume of the three dimensional space. The optical properties of the distal optic will define the optical axis range of focus for the slices and thus the relative volumetric dimensions of each slice. By collecting subsequent slices at depth intervals that were integer multiples of the optical depth of field of the distal lenses, the accuracy of the final measured volume. As the interval between the collected slices is increased, the accuracy will be decrease. If the rate of change in the interior perimeter occurs more often that the slices are collected, an error in the actual versus calculated volume will occur. If the interval between slices is closer to the optical depth of field of the distal optic, there is less of a chance of missing a change in the perimeter of the interior. The additional slices of data 2-9 are optical slices of data taken at known intervals and with measures of the optical depth of focus of the optical rigid fiberscope or flexible endoscope 11. This provides a very accurate determination of the volume of the interior cavity 12. It also provides a method of determining the interior perimeter shape of the cavity 12.

The system 10 has use in both industrial and medical applications. Uses in the industrial realm include measuring the interior volume of small gas/liquid valves or odd shaped gas/liquid reservoirs to accurately determine the amount of a fluid is present within a liquid delivery system. Knowing the amount of gas/fluid within odd shaped valve will improve the accuracy of delivery of toxic, rare or expensive fluid mixtures. In the medical field, the system 10 can be used to measure the amount of tissue removed in a spinal discectomy procedure or the amount of bone marrow removed during a marrow transplant procedure. The system 10 can also be used to map the interior perimeter shape and size of the hole generated during a hip or knee replacement. With an accurate measure of the interior of the receiving hole for a prosthesis, that data can be fed into a computer numerical machining mill to improve the fit of the device.

Figure 2:
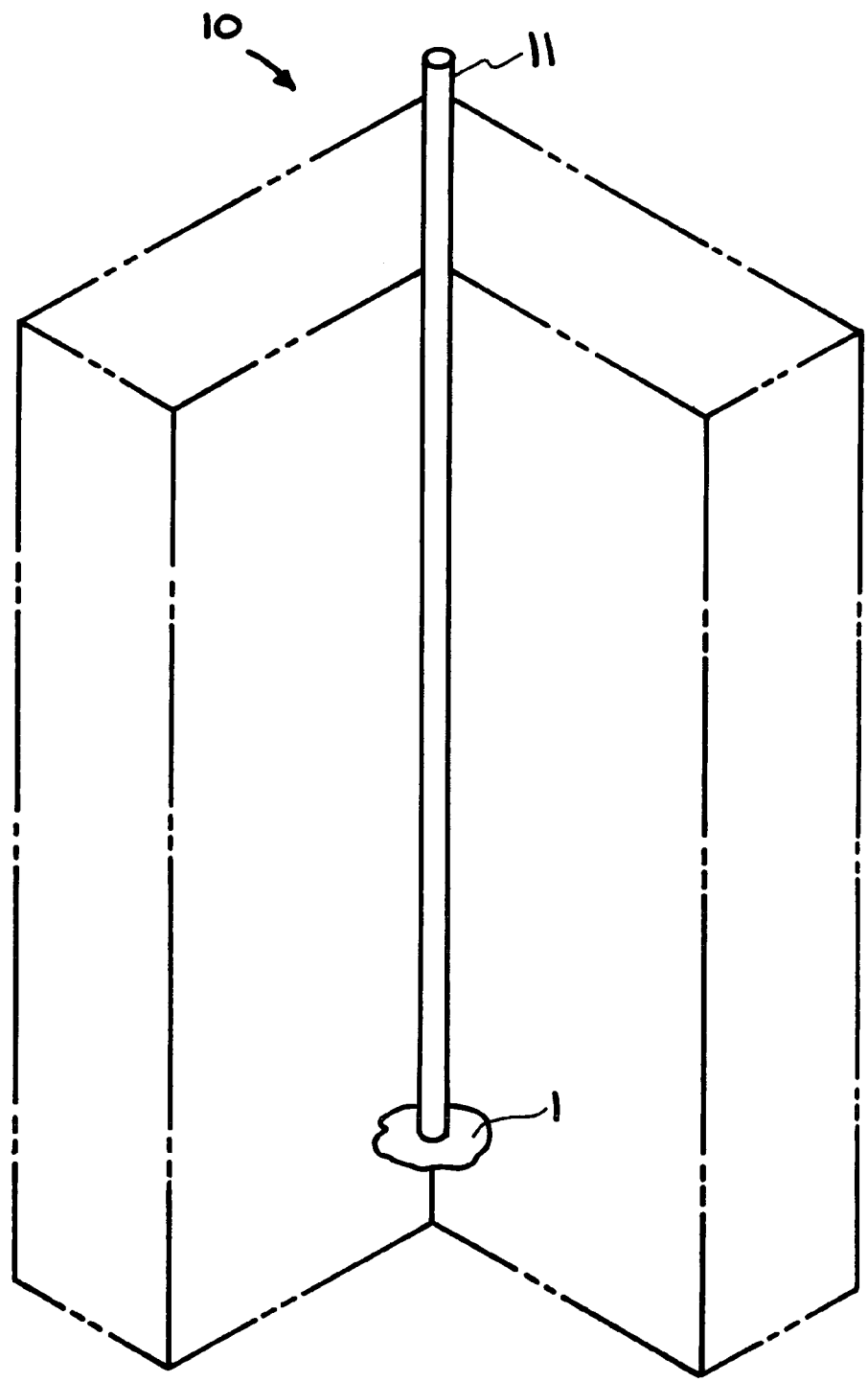
FIG. 2 illustrates the initial step of the method for measuring the three-dimensional volume and perimeter shape of an interior cavity of the resent invention.

Referring now to FIG. 2, one step of the method for measuring the three-dimensional volume and perimeter shape of an interior cavity of the resent invention is illustrated. The high resolution, low optical distortion, narrow depth of field rigid fiberscope or flexible endoscope 11 is used to collect optical slices of data that represents a partial volume of the interior cavity 12. The interior cavity has a first edge which in this illustration is the bottom of the cavity 12. The interior cavity has a second edge positioned opposite the first edge, which in this illustration is the top of the cavity 12.

The high resolution, low optical distortion, narrow depth of field optical rigid fiberscope or flexible endoscope 11 is positioning at a first position at the first edge of the interior cavity. A first optical slice of data that represents a partial volume of the interior cavity is collected using the fiberscope or flexible endoscope 11 positioned at the first edge or bottom of the interior cavity 12. The first optical slice of data that represents a partial volume of the interior cavity 12 is designated by the reference numeral 1.

Subsequently the high resolution, low optical distortion, narrow depth of field rigid fiberscope or flexible endoscope 11 will be moved a number of incremental distances into the cavity to collect additional optical slices of data that represents partial volumes of the interior cavity.

Figure 3:
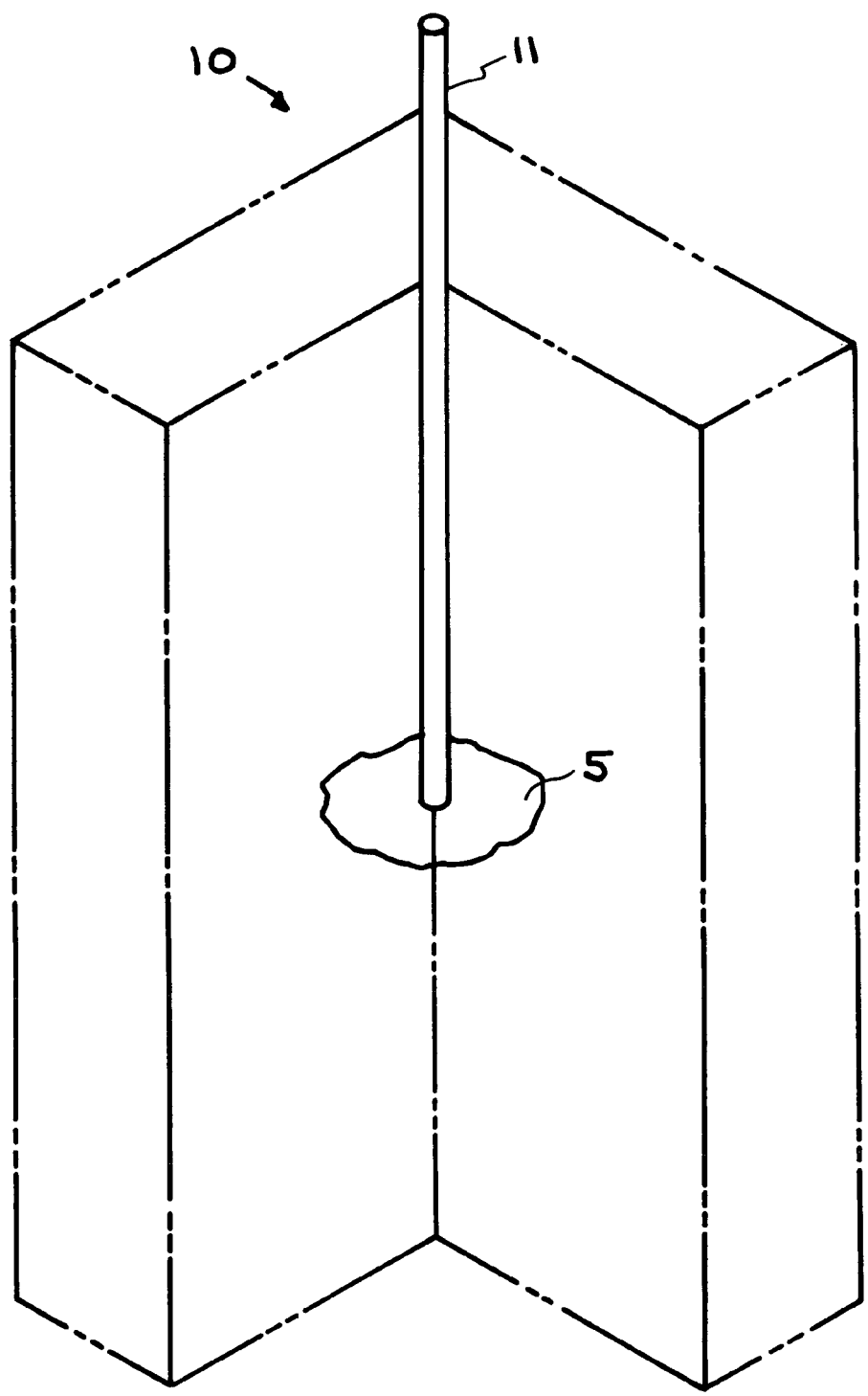
FIG. 3 illustrates an intermediate step of the method for measuring the three-dimensional volume and perimeter shape of an interior cavity of the resent invention.

Referring now to FIG. 3, an intermediate step of the method for measuring the three-dimensional volume and perimeter shape of an interior cavity of the resent invention is illustrated. The high resolution, low optical distortion, narrow depth of field rigid fiberscope or flexible endoscope 11 is shown drawn upward in the interior cavity 12 intermediate between the first edge or bottom and the second edge or top of the cavity 12. An intermediate optical slice of data that represents a partial volume of the interior cavity is collected using the fiberscope or flexible endoscope 11. The intermediate optical slice of data is designated by the reference numeral 5. Subsequently the rigid fiberscope or flexible endoscope 11 will be moved additional incremental distances into the cavity to collect additional optical slices of data that represents partial volumes of the interior cavity.

Figure 4:
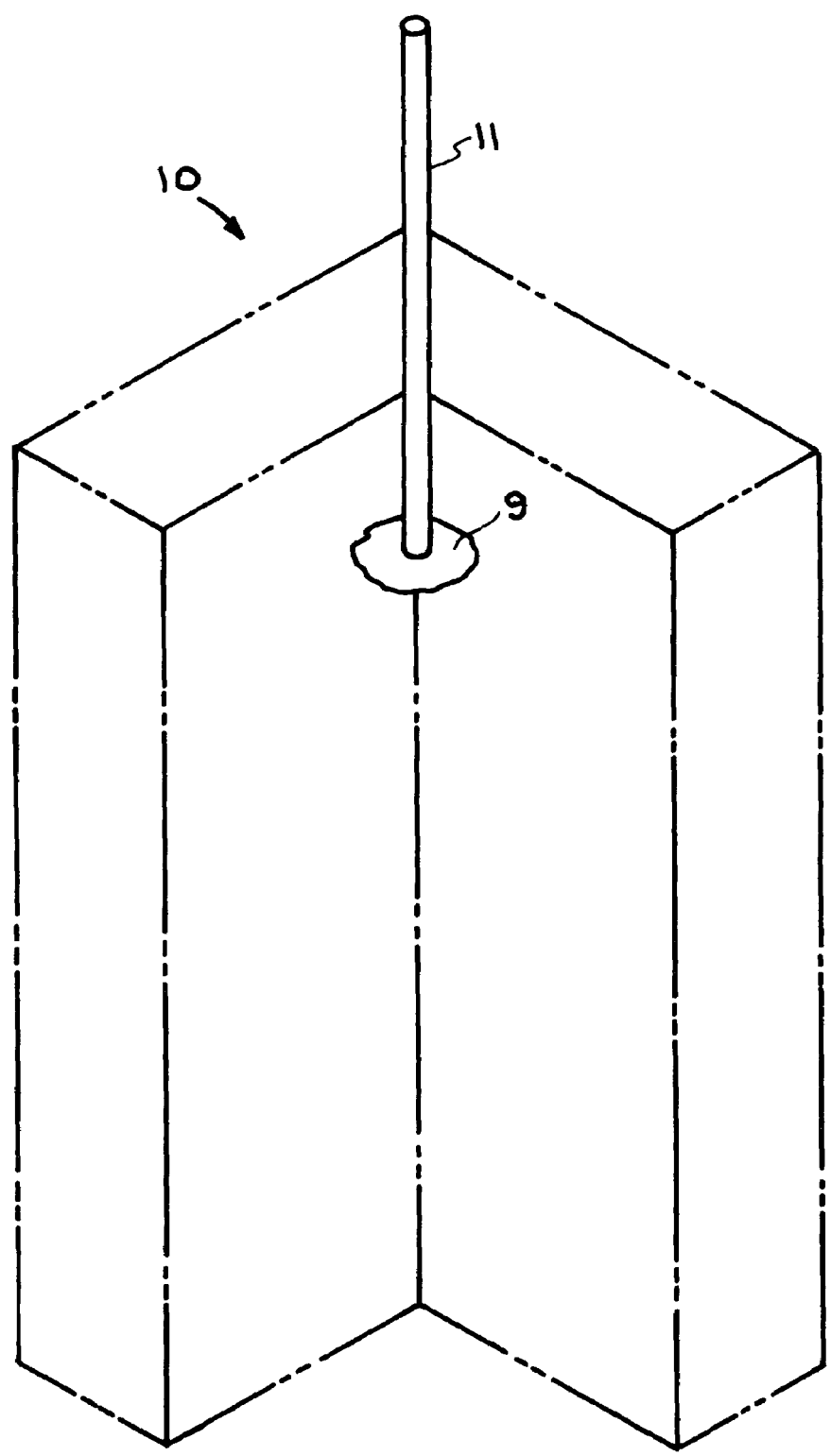
FIG. 4 illustrates one of the final steps of the method for measuring the three-dimensional volume and perimeter shape of an interior cavity of the resent invention.

Referring now to FIG. 4, another step of the method for measuring the three-dimensional volume and perimeter shape of an interior cavity of the resent invention is illustrated. The high resolution, low optical distortion, narrow depth of field rigid fiberscope or flexible endoscope 11 is shown drawn upward in the interior cavity 12 to the second edge or top of the cavity 12. An intermediate optical slice of data that represents the final volume of the interior cavity is collected using the fiberscope or flexible endoscope 11. The final optical slice of data is designated by the reference numeral 9.

Referring again to FIGS. 1, 2, 3, and 4; the system 10 is described in greater detail. The system 10 will optically measure the lateral size and 3-Dimensional volume of the interior cavity 12 and the perimeter shape of the cavity using the high resolution, low optical distortion, narrow depth of field rigid fiberscope or flexible endoscope 11. The optic 11 is designed to have a very shallow optical depth of focus, with high spatial resolution and low optical distortion.

The optical instrument 11 is inserted into the cavity 12 to be measured at a depth where the base or furthest extent of the cavity 12 to be measured is in good focus. An image 1 at that base or initial optical plane is collected with an electronic or other sensing device to make a permanent record of the image plane 1. The instrument 11 is pulled out of the space a known distance and another image set 2 is collected. In this fashion, next and subsequent images 3-9 are collected.

Only a narrow portion of the image 1 will be in sharp focus. Using computer software, the image 1 data is processed and the out of focus data is filter out retaining only the perimeter of the interior volume that is in good focus. Using that perimeter and the distance between the image slices, a calculation of the interior volume of the cavity 12 is determined.

If the optical instrument is a rigid bore scope and the rate of removal synchronized to a fixed rate, relative to the digital camera rate, the image slices volumes can be taken at fixed rates. With the fixed rate of image collection, the process can be partially automated. If the imaging system has a sufficiently narrow depth of focus and that can be synchronized to the camera frame rate and the imaging system withdrawal rate, a set of very thin in focus images sets can be collected much like computer tomography slices are collected. The processed data slices can be put into commercial computer tomography or 3-D analysis software packages allowing volume calculations and other properties of the cavity that was measured can be calculated.

The optic 11 is designed to cover the area in question with high spatial resolution, low optical distortion and narrow optical depth of focus. With the lens system 11, a rigid borescope or a flexible endoscope can be used to collect thin optical slices of data that represent partial volumes of the cavity being measured. With careful collection of the slices at known intervals and a measure of the optical depth of focus of the imaging system, a very accurate determination of the volume of the interior cavity 12 can be obtained.

Figure 5:
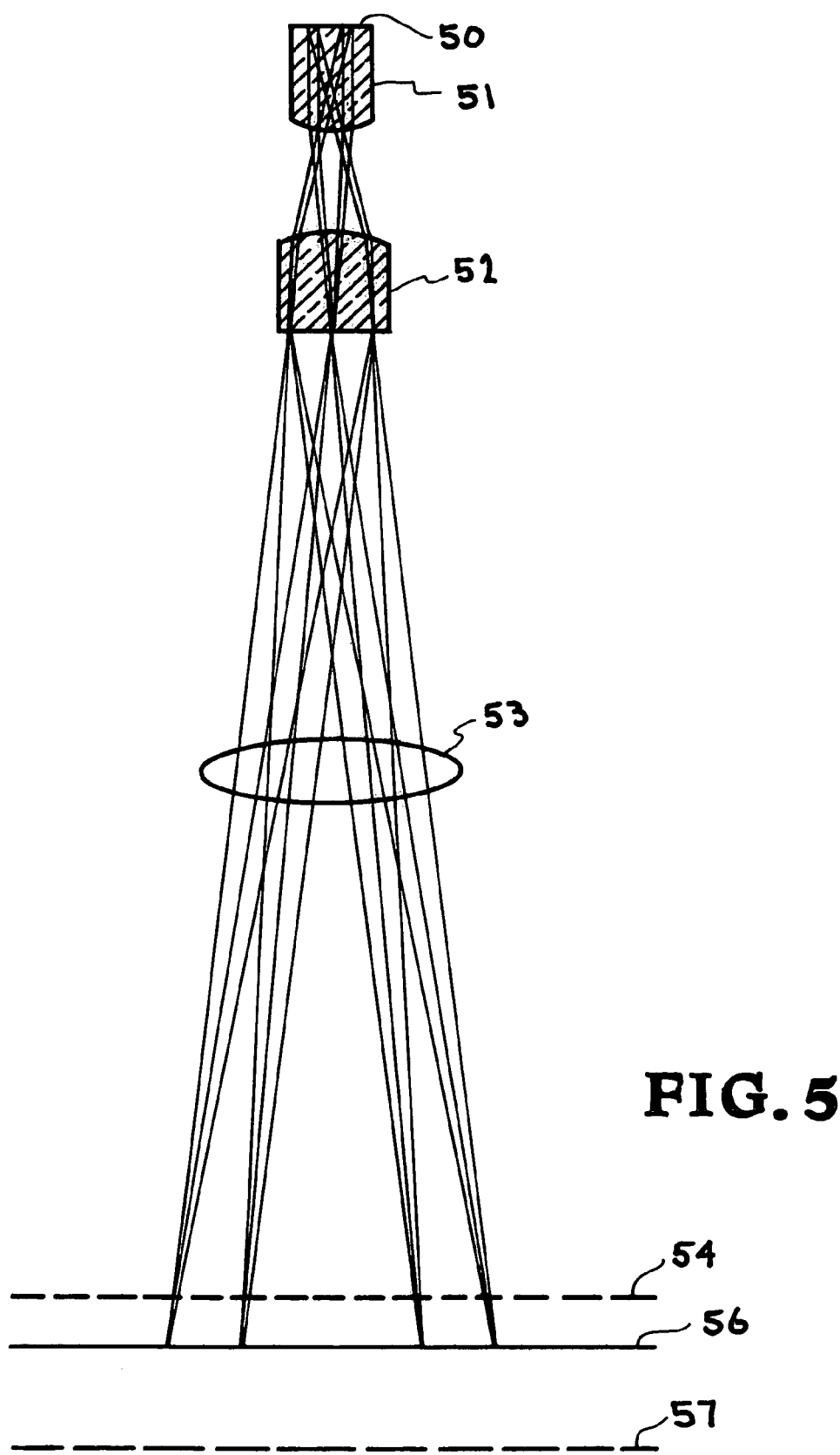
FIG. 5 is a representation of the optical slices.

Referring now to FIG. 5 a representation of the optical slices is shown. The endoscope or borescope has a distal end optic that in reality has a fairly narrow optical angle of ~10 degrees. That would generate a conical image that would encompass the perimeter image plane. The plots show the endoscope and not the image field of the lens. This is a plot from the optical design code ZEMAX that has a cross section of a simple lens design with a 5 mm front working distance between the lens and the object. If this were pointed down into an interior cavity, the rays of light would describe a cone.

FIG. 5 illustrates a system of measuring the perimeter shape of an interior cavity. The interior cavity has a first edge at a position in the interior cavity and a second edge positioned opposite the first edge. The system includes the following optical components:

Component 50—An image plane 50 that would present the image of the test object cavity plane slice to either the distal end of a flexible fiber optic endoscope or a rigid borescope.

Component 51—A single element image forming optic 51, or

Component 52—Multiple element imaging optics 52

Component 53—Image forming ray bundles.

The single element image forming optic 51, or the multiple element imaging optics 52 would collect the image light from and bring it into a focused image at the image plane 50. The image rays collected by the image forming optical element(s) 51, 52 would pass from the object plane slice thru a finite space and impinge upon the image forming optic(s) 51, 52 and be focused onto the image plane 50. The object plane slice would be in best focus at a fixed distance 56 from the image plane 50 and a fractional region represented by the space between the near 54 and far 56 ends of the object depth of focus would be in an acceptable image focus as to be recognizable as representing the depth of focus region for the image forming optics. Then the individual volumetric slice collected by this optical system would be defined by the geometric space bounded perimeter of the near in-focus plane at one end and the far in-focus plane at the other end. Thus a finite depth, vertical planar slice of the interior cavity will be collected by the imaging system at any given point along the trajectory of the image collection system for each image collected 57.

The system 10 has use in both industrial and medical applications. Uses in the industrial realm include measuring the interior volume of small gas/liquid valves or odd shaped gas/liquid reservoirs to accurately determine the amount of a fluid is present within a liquid delivery system. Knowing the amount of gas/fluid within odd shaped valve will improve the accuracy of delivery of toxic, rare or expensive fluid mixtures. In the medical field, the system 10 can be used to measure the amount of tissue removed in a spinal discectomy procedure or the amount of bone marrow removed during a marrow transplant procedure. The system 10 can also be used to map the interior perimeter shape and size of the hole generated during a hip or knee replacement. With an accurate measure of the interior of the receiving hole for a prosthesis, that data can be fed into a computer numerical machining mill to improve the fit of the device.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for measuring the perimeter shape of an interior cavity, said interior cavity having a first edge at a position in said interior cavity and a second edge positioned opposite said first edge, comprising:

an image plane that presents the image of a test object cavity plane slice to either the distal end of a flexible fiber optic endoscope or a rigid borescope, a single element image forming optic that collects the image light and brings it into a focused image at said image plane, the image rays collected by the image forming optical element passing from the object plane slice thru a finite space and impinge upon the image forming optic and be focused onto said image plane, the object plane slice being in best focus at a fixed distance from said image plane and a fractional region represented by the space between the near and far ends of an object depth of focus being in an acceptable image focus as to be recognizable as representing the depth of focus region for said image forming optic, the individual volumetric slice collected by an optical system being defined by a geometric space bounded perimeter of a near in-focus plane at one end and a far in-focus plane at the other end, a finite depth, vertical planar slice of the interior cavity being collected by an imaging system at any given point along a trajectory of an image collection system for each image collected.

* * * * *